United States Patent
Chen et al.

(10) Patent No.: US 9,451,934 B2
(45) Date of Patent: Sep. 27, 2016

(54) METHOD, APPARATUS, AND ULTRASONIC MACHINE FOR GENERATING A FUSED ULTRASONIC IMAGE

(71) Applicant: General Electric Company, Schenectady, NY (US)

(72) Inventors: Dongqing Chen, Wauwatosa, WI (US); Jiajiu Yang, Wuxi (CN); Menachem Halmann, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/553,147

(22) Filed: Nov. 25, 2014

(65) Prior Publication Data
US 2015/0150539 A1    Jun. 4, 2015

(30) Foreign Application Priority Data
Nov. 29, 2013    (CN) .......................... 2013 1 0631479

(51) Int. Cl.
| | | |
|---|---|---|
| G06K 9/00 | (2006.01) | |
| A61B 8/08 | (2006.01) | |
| A61B 8/00 | (2006.01) | |

(52) U.S. Cl.
CPC .......... *A61B 8/5253* (2013.01); *A61B 8/5223* (2013.01); *A61B 8/461* (2013.01); *A61B 8/468* (2013.01); *A61B 8/469* (2013.01); *A61B 8/5207* (2013.01)

(58) Field of Classification Search
USPC ............................................... 382/128–134
See application file for complete search history.

(56) References Cited

U.S. PATENT DOCUMENTS

| | | | | |
|---|---|---|---|---|
| 5,899,864 | A * | 5/1999 | Arenson | ............ G01S 15/8979 600/453 |
| 8,270,691 | B2 | 9/2012 | Xu et al. | |
| 2009/0092298 | A1 * | 4/2009 | Xu | ........................ G06T 7/0028 382/128 |
| 2009/0161938 | A1 * | 6/2009 | Shekhar | ............... A61B 8/0883 382/131 |
| 2010/0185091 | A1 * | 7/2010 | Sumi | ....................... A61B 8/08 600/443 |
| 2010/0222680 | A1 * | 9/2010 | Hamada | ................... A61B 8/06 600/443 |
| 2010/0268088 | A1 * | 10/2010 | Prus | ........................ A61B 8/14 600/459 |
| 2011/0066031 | A1 * | 3/2011 | Lee | .......................... A61B 8/13 600/443 |
| 2012/0010501 | A1 * | 1/2012 | Cerofolini | .............. A61B 5/055 600/427 |
| 2012/0069020 | A1 * | 3/2012 | Smith-Casem | ......... G06T 15/08 345/426 |
| 2012/0078101 | A1 * | 3/2012 | Kim | ..................... A61B 8/0866 600/443 |
| 2012/0078102 | A1 * | 3/2012 | Lee | ..................... A61B 8/0866 600/443 |

FOREIGN PATENT DOCUMENTS

WO    2013001439 A2    1/2013

* cited by examiner

*Primary Examiner* — Alex Liew
(74) *Attorney, Agent, or Firm* — GE Global Patent Operation; Marc A. Vivenzio

(57) ABSTRACT

The present invention relates to a method, apparatus, and ultrasonic machine for generating a fused ultrasonic image. The method comprises extracting an anatomical location from a stored ultrasonic image, and generating the fused ultrasonic image according to the anatomical location and a currently obtained ultrasonic image. The apparatus comprises an extraction module for extracting an anatomical location from a stored ultrasonic image, and a generation module for generating the fused ultrasonic image according to the anatomical location and a currently obtained ultrasonic image.

13 Claims, 2 Drawing Sheets

METHOD, APPARATUS, AND ULTRASONIC MACHINE FOR GENERATING A FUSED ULTRASONIC IMAGE

TECHNICAL FIELD OF THE INVENTION

This invention relates to method and apparatus for processing ultrasonic images, and more particularly to a method, apparatus, and corresponding ultrasonic machine for generating a fused ultrasonic image.

BACKGROUND OF THE INVENTION

In the current clinical application, an ultrasonic machine may be used to recheck the same region of a subject. To compare examination results made at different times, generally ultrasonic images obtained from each examination are stored such that the required image previously generated can be easily read and displayed when comparison is necessary during the next examination.

To ensure comparability of two examination results, the ultrasonic image of the current examination and that obtained from the previous examination should relate to the same region of the subject, which largely depends upon the clinical operation experience of the doctor, namely, how to accurately operate an ultrasonic probe. It is a challenge to those inexperienced doctors.

In general, consistency between anatomical locations on images from two examinations can help to determine whether said two images are generated from the same region of the subject. The anatomical location mentioned herein can be locations of the subject's organs such as bones and ligaments on the image.

However, in the prior art, doctors have to observe by themselves anatomical locations on two images to determine the consistency therebetween. The accuracy cannot be ensured.

Therefore, a method, apparatus, and ultrasonic machine for generating the fused ultrasonic images are in demand to extract the anatomical location from the available ultrasonic image and fuse it onto the real-time ultrasonic image in a current examination to thus generate a fused ultrasonic image which tells the user whether the currently obtained ultrasonic image and the previous ultrasonic image are generated based on the same region of the subject.

SUMMARY OF THE INVENTION

One embodiment of this invention provides a method of generating a fused ultrasonic image, comprising: extracting an anatomical location from a stored ultrasonic image; and generating the fused ultrasonic image according to the anatomical location and a currently obtained ultrasonic image.

Another embodiment of this invention provides an apparatus for generating a fused ultrasonic image, comprising: an extraction module for extracting an anatomical location from a stored ultrasonic image; and a generation module for generating the fused ultrasonic image according to the anatomical location and a currently obtained ultrasonic image.

Still another embodiment of this invention provides an ultrasonic machine, comprising the apparatus for generating the fused ultrasonic image according to the present invention.

SUMMARY OF THE DRAWINGS

The present invention will be more apparent to those skilled in the art upon reading the following detailed description of embodiments with reference to the accompanying drawings.

DETAILED DESCRIPTION OF THE INVENTION

Some specific embodiments of the present invention will be described hereinafter. However, it should be noted that it is impossible to elaborate on all the features of a specific embodiment for sake of clarity and conciseness. It should be understood that in practical implementation of any embodiment, as is in any engineering or designing process, a variety of particular decisions and changes from one implementation to another would often be made, in order to achieve the developers' specific goals, or to meet system-related, or business-related constraints. It should be also understood that, although such development process may involve complicated and time-consuming endeavors, certain modifications to the design, manufacture or production on the basis of the present disclosure are nothing but conventional technical means for a skilled artisan in the related field, and the present disclosure should not be construed as being insufficient.

Unless otherwise defined, the technical terms or scientific terms used in the claims and the description should have a usual meaning generally understood by those having ordinary skills in the art to which the present invention relates. The wordings "first", "second" and the like used in the description and the claims are not intended to indicate any order, quantity, or importance, but to distinguish between different components. The words "a", "an" and the like do not mean quantitative restrictions, but presence of at least one. The words "comprising", "including" and the like mean that an element or object before these words covers an element, object or equivalents listed after these words, but do not exclude presence of other element or object. "Connect to" or "connect with" and other similar wordings are not limited to physical or mechanical connections, nor are they limited to direct or indirect connections.

To make the objects, technical solutions and advantages of the present invention more apparent, the technical solution of the present invention will be described in a clear and complete manner in combination with specific embodiments and corresponding drawings. Evidently, these embodiments are only part of, not all embodiments of the present invention. Any other embodiment obtained by a person ordinary skilled in the art without inventive labor on the basis of these embodiments will fall within the scope of the present invention.

According to embodiments of the present invention, there is provided a method for generating fused ultrasonic images.

Figure 1:
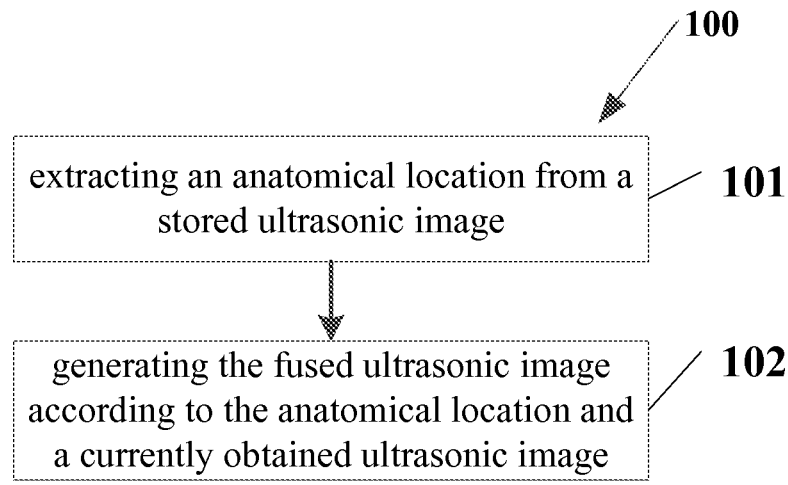
FIG. 1 is a flow diagram illustrating one embodiment of a method for generating a fused ultrasonic image according to the present invention.

Reference is made to FIG. 1, which is a flow diagram illustrating one embodiment of a method 100 for generating fused ultrasonic images according to the present invention.

As shown in FIG. 1, at step 101, the anatomical location is extracted from a stored ultrasonic image The stored ultrasonic image herein may be the one to be compared with the image obtained from the current examination. Generally speaking, it can be a stored image generated from a previous ultrasonic examination which concerns the same region of the same patient.

The extracted anatomical location can be a position of a region which can be apparently distinguished from organs and tissues therearound on the ultrasonic images, for example, positions of such organs as bones and ligaments on the ultrasonic images.

In one embodiment of the present invention, extraction of the anatomical location can be implemented by analyzing the pixel values of pixel points of the stored B-mode ultrasonic images.

Figure 2:
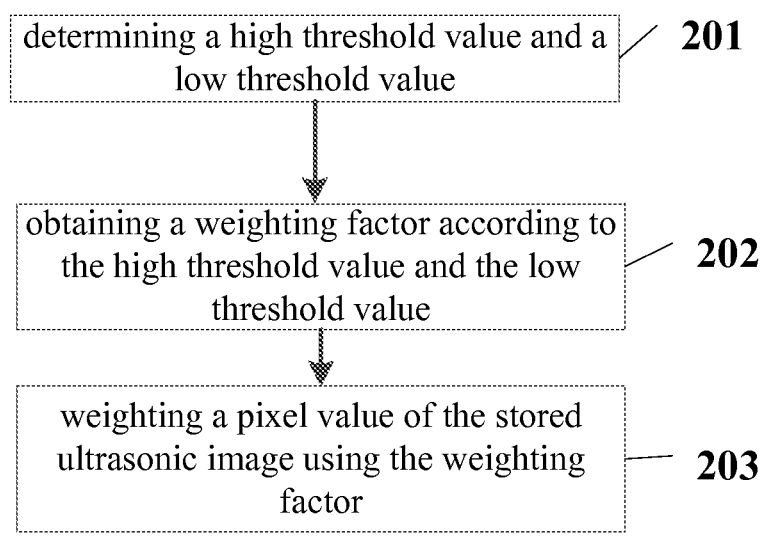
FIG. 2 is a flow diagram illustrating one embodiment of extraction of the required anatomical location from the stored ultrasonic image during the process of generating a fused ultrasonic image according to the present invention.

Reference is made to FIG. 2, which is a flow diagram illustrating one embodiment of extraction of the required anatomical location from the stored ultrasonic image (step 101) during the process of generating a fused ultrasonic image according to the present invention.

At step 201, a high threshold value and a low threshold value are determined.

In one embodiment of the present invention, the low threshold value can be determined based on the doctor preset proportion of the anatomical location to the stored ultrasonic image. That is, the low threshold value varies with the ultrasonic image. For example, if doctors intend to extract 20% pixel points with the maximum pixel values as the anatomical location from the stored ultrasonic images, they can determine the lowest pixel value among the 20% pixel points with the maximum pixel values by analyzing the diagram illustrating distribution of pixel values of stored ultrasonic images and use it as the low threshold value. In another embodiment of the present invention, the high threshold can also be set as a fixed value.

In one embodiment of the present invention, the high threshold value is determined based on the doctor preset proportion of the unaltered portion of the anatomical location to the stored ultrasonic image. That is, the high threshold value varies with the ultrasonic image. For example, if doctors intend to extract 5% pixel points with the maximum pixel values from the stored ultrasonic images and keep using said values for subsequent generation of fused images, they can determine the lowest pixel value among the 5% pixel points with the maximum pixel values by analyzing the diagram illustrating distribution of pixel values of stored ultrasonic images and use it as the high threshold value. In another embodiment of the present invention, the high threshold can also be set as a fixed value.

At step 202, a weighting factor is obtained according to the high and low threshold values.

The weighting factor can weight pixel values of the stored ultrasonic image and the currently obtained ultrasonic image. The weighting factor can be set according to each pixel point of the ultrasonic image.

In one embodiment of the present invention, the weighting factor of a pixel point can be determined based on the relations between the pixel value of each pixel point of the stored ultrasonic images and the high and low threshold values.

In one embodiment of the present invention, if the pixel value of the stored ultrasonic image is larger than or equal to the high threshold value, the weighting factor may be 1; if the pixel value of the stored ultrasonic image is smaller than or equal to the low threshold value, the weighting factor may be 0.

If the pixel value of the stored ultrasonic image is between the high threshold value and the low threshold value, the weighting factor is between 0 and 1 and is positively correlated to the pixel value. In one non-limiting embodiment, under such circumstances, the weighting factor can be obtained through the following formula:

$$\text{Weighting factor} = (\text{pixel value of the stored ultrasonic image} - \text{low threshold value})/(\text{high threshold value} - \text{low threshold value}).$$

In this way, the weighting factor can be limited between 0 and 1 and is positively correlated with the pixel value.

At step 203, the weight factor is used to weight the pixel value of the stored ultrasonic image.

The weighting factor directed to each pixel point obtained at step 202 is used to weight pixel values of all pixel points of the stored ultrasonic image.

As can be seen, for those pixel points having pixel values smaller than or equal to the low threshold value, the pixel values thereof become 0 after weighting; for those pixel points having pixel values larger than or equal to the high threshold value, the pixel values thereof remain unchanged after weighting. For those pixel points having pixel values between the high and low threshold values, the pixel values thereof decrease accordingly after weighting. The bigger the pixel value is, the smaller the reduced proportion is; the smaller the pixel value is, the bigger the reduced proportion is.

Thus, the desired histological location can be extracted from the stored ultrasonic images with unnecessary information removed.

At step 102, a fused ultrasonic image is generated according to the anatomical location and the currently obtained ultrasonic image.

A fused ultrasonic image can be generated by fusing the anatomical location extracted at step 101 onto the currently obtained ultrasonic image in a proper manner. For example, the anatomical location extracted at step 101 is superposed onto the currently obtained real-time B-mode ultrasonic image according to the pre-defined colors to generate a fused ultrasonic image, such that the doctor can conveniently make a comparison and check whether the scanned regions and planes are the same as those of the previous scan. The fused ultrasonic image comprises both the fixedly displayed anatomical location extracted at step 101 and the B-mode ultrasonic image displayed in real-time. When the anatomical location on the real-time B-mode ultrasonic image and the anatomical location fixedly displayed with colors on a screen match together, regions of two scans can be considered as the same.

Figure 3:
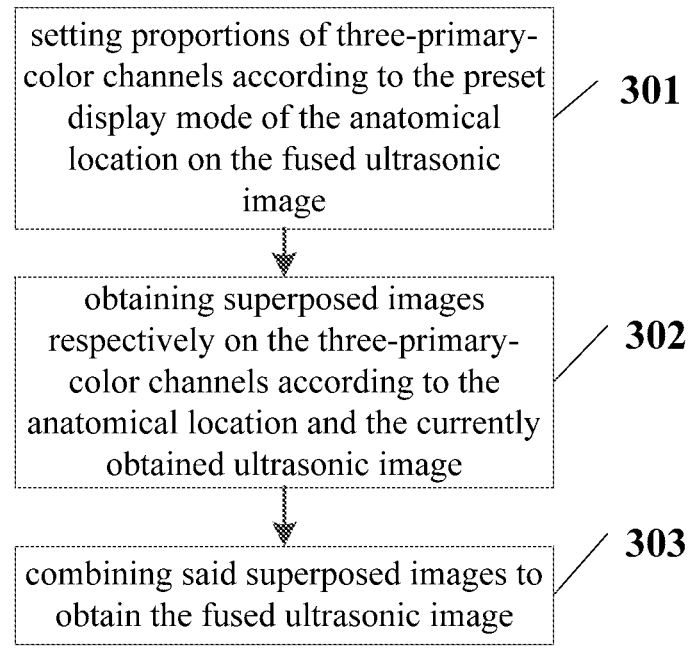
FIG. 3 is a flow diagram illustrating one embodiment of generation of the fused ultrasonic image based on the anatomical location and a currently obtained ultrasonic image during the process of generating a fused ultrasonic image according to the present invention.

Reference is made to FIG. 3, which is a flow diagram illustrating one embodiment of generation of the fused ultrasonic image according to the anatomical location and a currently obtained ultrasonic image (step 102) during the process of generating a fused ultrasonic image according to the present invention.

At step 301, proportions of three-primary-color channels are set according to the preset display mode of the anatomical location on the fused ultrasonic image.

Weighting of three-primary-color channels can be adjusted according to the preset display mode of the anatomical location extracted at step 101 on the fused ultrasonic image. For example, if the anatomical location extracted at step 101, as pre-defined, is displayed in purple on the fused ultrasonic image, the weight coefficient of three channels can be adjusted according to combination and overlapping principle of three primary colors such that the overlapped three-primary-color images can be displayed in purple.

At step 302, superposed images are obtained respectively on the three-primary-color channels according to the anatomical location and the currently obtained ultrasonic image.

In one embodiment of the present invention, the weighting process at step 203 and the superposition process at step 302 can be completed at one time.

In a non-limiting embodiment, the following formulas can be used to complete steps 203 and 302 at one time, wherein, old_img represents the stored ultrasonic image, new_img represents the currently obtained ultrasonic image, and opacity_factor represents the weighting factor at step 202.

fusion_img(R)=f(opacity_factor, old_img, new_img, C_R)

fusion_img(G)=f(opacity_factor, old_img, new_img, C_G)

fusion_img(B)=f(opacity_factor, old_img, new_img, C_B)

In said formulas, C_R, C_G, and C_B represent proportions of the three-primary-color channels set at step 301 and f( ) represents the superposed images obtained by applying the weighting factor opacity_factor to the stored ultrasonic image and the currently obtained ultrasonic image with proportions of three-primary-color channels taken into consideration.

At step 303, the fused ultrasonic image is obtained by combining the superposed images.

The final desired fused ultrasonic image can be obtained by combining the superposed images on the three-primary-color channels obtained at step 302.

On the fused ultrasonic image, the anatomical location information in the stored ultrasonic images is fixedly displayed using the pre-set color (e.g., purple) and the currently obtained real-time ultrasonic images are also retained and displayed.

In one embodiment of the present invention, position information of the region of interest (ROI) can be read from the stored ultrasonic image and then be displayed on the currently obtained ultrasonic image.

When the fused ultrasonic image is generated, position information of the region of interest can be read from the stored ultrasonic image, for example, position coordinate values of the region of interest. Then said information is automatically copied onto the currently obtained real-time ultrasonic image and said region can be sketched with an eye-catching color such as yellow.

What is hitherto described is a method for generating a fused ultrasonic image according to embodiments of the present invention. According the method of this invention, the anatomical location of the existing ultrasonic image can be extracted and fused onto the real-time displayed ultrasonic image during the current examination to generate the fused ultrasonic image which tells the user whether the currently obtained ultrasonic image and the existing ultrasonic image relate to the same region of the subject. The method of the present invention can also automatically remind the user of the determined region of interest of the previous examination and automatically copy said region to the same position of the real-time image of the current examination to thus avoid errors caused by the doctor's manual operation during the process of redetermining the same region of interest.

Similar to said method, the present invention also provides a corresponding apparatus.

Figure 4:
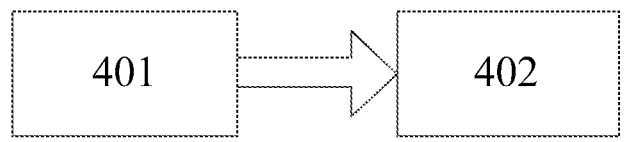
FIG. 4 is a schematic block diagram illustrating one embodiment of an apparatus for generating fused ultrasonic images according to the present invention.

FIG. 4 is a schematic block diagram illustrating one embodiment of an apparatus 400, said apparatus being an ultrasonic machine configured for generating fused ultrasonic images according to the present invention.

As shown in FIG. 4, the apparatus 400 comprises an extraction module 401 for extracting an anatomical location from a stored ultrasonic image; and a generation module 402 for generating the fused ultrasonic image according to the anatomical location and a currently obtained ultrasonic image.

In one embodiment of the present invention, the extraction module 401 may further comprise: a threshold value determination module for determining a high threshold value and a low threshold value; a weighting factor determination module for obtaining a weighting factor according to the high threshold value and the low threshold value; and a weighting module for weighting a pixel value of the stored ultrasonic image using said weighting factor.

In one embodiment of the present invention, the generation module 402 further comprises: a channel proportion setting module for setting proportions of three-primary-color channels according to the preset display mode of the anatomical location on the fused ultrasonic image; a superposition module for obtaining superposed images respectively on the three-primary-color channels according to the anatomical location and the currently obtained ultrasonic image; and a combination module for combining said superposed images to obtain the fused ultrasonic image.

In one embodiment of the present invention, the apparatus 400 may further comprise: a region of interest display module for reading position information of the region of interest on the stored ultrasonic image and displaying said information on the currently obtained ultrasonic image.

What is hitherto described is an apparatus for generating a fused ultrasonic image according to embodiments of the present invention. Similar to said method, according the apparatus of this invention, the anatomical location of the existing ultrasonic image can be extracted and fused onto the real-time displayed ultrasonic image during the current examination to generate the fused ultrasonic image which tells the user whether the currently obtained ultrasonic image and the existing ultrasonic image relate to the same region of the subject. The apparatus of the present invention can also automatically remind the user of the determined region of interest of the previous examination and automatically copy said region to the same position of the real-time image of the current examination to thus avoid errors caused by the doctor's manual operation during the process of redetermining the same region of interest.

As one skilled in the art would appreciate, the apparatus 400, being an ultrasonic machine, inherently includes a processor with a memory for operating the aforementioned modules.

While the present invention has been described in detail with reference to specific embodiments, a skilled person will understand that the present invention is not limited to said embodiments. For those skilled in the art, various modifications and variations may be made to the present invention. Any modification, substitution, improvement or the like

What is claimed is:

1. A method of generating a fused ultrasonic image, comprising:
    extracting an anatomical location from a stored ultrasonic image by at least:
    determining a high threshold value and a low threshold value;
    obtaining a weighting factor according to the high threshold value and the low threshold value, wherein (i) if the pixel value is larger than or equal to the high threshold value, the weighting factor is 1, (ii) if the pixel value is smaller than or equal to the low threshold value, the weighting factor is 0, and (iii) if the pixel value is between the high threshold value and the low threshold value, the weighting factor is between 0 and 1 and is positively correlated to the pixel value; and
    weighting a pixel value of the stored ultrasonic image using said weighting factor; and
    generating the fused ultrasonic image according to the anatomical location and a currently obtained ultrasonic image.

2. The method according to claim 1, wherein the low threshold value is determined based on a doctor preset proportion of the anatomical location to the stored ultrasonic image and the high threshold value is determined based on a doctor preset proportion of the unaltered portion of the anatomical location to the stored ultrasonic image.

3. The method according to claim 1, wherein the step of generating the fused ultrasonic image according to the anatomical location and the currently obtained ultrasonic image further comprises:
    setting proportions of three-primary-color channels according to the preset display mode of the anatomical location on the fused ultrasonic image;
    obtaining superposed images respectively on the three-primary-color channels according to the anatomical location and the currently obtained ultrasonic image; and
    combining said superposed images to obtain the fused ultrasonic image.

4. The method according to claim 1, further comprising:
    reading position information of the region of interest on the stored ultrasonic image and displaying said information on the currently obtained ultrasonic image.

5. The method according to claim 1, further comprising:
    reading position information of the region of interest on the stored ultrasonic image and displaying said information on the currently obtained ultrasonic image.

6. The method according to claim 2, further comprising:
    reading position information of the region of interest on the stored ultrasonic image and displaying said information on the currently obtained ultrasonic image.

7. The method according to claim 1 further comprising:
    reading position information of the region of interest on the stored ultrasonic image and displaying said information on the currently obtained ultrasonic image.

8. The method according to claim 3, further comprising:
    reading position information of the region of interest on the stored ultrasonic image and displaying said information on the currently obtained ultrasonic image.

9. An ultrasonic machine, comprising:
    an extraction module for extracting an anatomical location from a stored ultrasonic image;
    a threshold value determination module for determining a high threshold value and a low threshold value;
    a weighting factor determination module for obtaining a weighting factor according to the high threshold value and the low threshold value, wherein (i) if the pixel value is larger than or equal to the high threshold value, the weighting factor is 1, (ii) if the pixel value is smaller than or equal to the low threshold value, the weighting factor is 0, and (iii) if the pixel value is between the high threshold value and the low threshold value, the weighting factor is between 0 and 1 and is positively correlated to the pixel value;
    a weighting module for weighting a pixel value of the stored ultrasonic image using said weighting factor; and
    a generation module for generating the fused ultrasonic image according to the anatomical location and a currently obtained ultrasonic image.

10. The ultrasonic machine according to claim 9, further comprising:
    a region of interest display module for reading position information of the region of interest in the stored ultrasonic image and displaying said information on the currently obtained ultrasonic image.

11. The ultrasonic machine according to claim 9, wherein the generation module further comprises:
    a channel proportion setting module for setting proportions of three-primary-color channels according to a preset display mode of the anatomical location on the fused ultrasonic image;
    a superposition module for obtaining superposed images respectively on the three-primary-color channels according to the anatomical location and the currently obtained ultrasonic image; and
    a combination module for combining said superposed images to obtain the fused ultrasonic image.

12. The ultrasonic machine according to claim 9, further comprising:
    a region of interest display module for reading position information of the region of interest in the stored ultrasonic image and displaying said information on the currently obtained ultrasonic image.

13. The ultrasonic machine according to claim 11, further comprising:
    a region of interest display module for reading position information of the region of interest in the stored ultrasonic image and displaying said information on the currently obtained ultrasonic image.

* * * * *